(12) United States Patent
Liu et al.

(10) Patent No.: US 11,975,099 B2
(45) Date of Patent: May 7, 2024

(54) ETHANOL FOAM SCLEROSING AGENT FOR TREATING VASCULAR ANOMALIES AND PREPARATION METHOD THEREOF

(71) Applicant: QILU HOSPITAL OF SHANDONG UNIVERSITY, Shandong (CN)

(72) Inventors: Shaohua Liu, Shandong (CN); Hanshu Zhang, Shandong (CN); Aijun Yang, Shandong (CN); Yiran Liu, Shandong (CN)

(73) Assignee: QILU HOSPITAL OF SHANDONG UNIVERSITY, Shandong (CN)

( * ) Notice: Subject to any disclaimer, the term of this patent is extended or adjusted under 35 U.S.C. 154(b) by 487 days.

(21) Appl. No.: 17/311,354

(22) PCT Filed: Dec. 11, 2019

(86) PCT No.: PCT/CN2019/124643
§ 371 (c)(1),
(2) Date: Jun. 7, 2021

(87) PCT Pub. No.: WO2020/238148
PCT Pub. Date: Dec. 3, 2020

(65) Prior Publication Data
US 2022/0023210 A1    Jan. 27, 2022

(30) Foreign Application Priority Data
May 28, 2019 (CN) .......................... 201910450705.6

(51) Int. Cl.
| | | |
|---|---|---|
| *A61K 9/12* | (2006.01) | |
| *A61K 31/045* | (2006.01) | |
| *A61K 47/10* | (2017.01) | |
| *A61K 47/24* | (2006.01) | |
| *A61K 47/26* | (2006.01) | |
| *A61K 47/36* | (2006.01) | |

(52) U.S. Cl.
CPC ............ *A61K 9/122* (2013.01); *A61K 31/045* (2013.01); *A61K 47/10* (2013.01); *A61K 47/24* (2013.01); *A61K 47/26* (2013.01); *A61K 47/36* (2013.01)

(58) Field of Classification Search
CPC ...... A61K 9/122; A61K 31/045; A61K 47/10; A61K 47/24; A61K 47/26; A61K 47/36; A61K 9/0019; A61P 9/14; A61P 35/00
See application file for complete search history.

(56) References Cited

U.S. PATENT DOCUMENTS

2016/0101881 A1* 4/2016 Wright ................ A61K 9/0019
128/202.16

FOREIGN PATENT DOCUMENTS

| CN | 1114193 | 1/1996 |
|---|---|---|
| CN | 1682693 | 10/2005 |
| CN | 103341182 | 10/2013 |
| CN | 103800278 | 5/2014 |
| CN | 106572973 | 4/2017 |

OTHER PUBLICATIONS

Wang, Weijie et al., "Treatment of Hemangioma with Local Injection of Absolute Ethanol.", Clinical Medicine. vol. 13, No. 2, Mar. 2, 1993, with English abstract. pp. 1-2.
Wu Qizhen et al., "Endovascular Treatment for Venous Malformations with Three-point Anhydrous Ethanol Injection", Journal of Central South University (Medical Science). vol. 40, No. 8, with English abstract. Aug. 15, 2015, pp. 1-5.
J. R. Torres-Lapasio et al., "Interpretive strategy for optimizaiton of surfactant and alcohol concentration in micellar liquid chromatography", Journal of Chromatography A., Dec. 31, 1994, pp. 239-253.
Zhang, Liangfen et al., "Alcohol Intake and Skin Vessel System.", Foreign Medical Sciences, Section ofDermatology and Venereology. vol. 27, No. 1, with English abstract. Feb. 15, 2001, pp. 1-4.
Hemangioma and Vascular Malformation Group of Plastic Surgery Branch of Chinese Medical Association, "Guidelines for the Diagnosis and Treatment of Hemangiomas and Vascular Malformations (2016 Edition)", Journal of Tissue Engineering and Reconstructive Surgery. vol 12, No. 2, Apr. 15, 2016, with English abstract. pp. 1-33.
Dong Jinbin et al., "Ultrasound-guided cinnamyl alcohol and absolute ethanol sclerotherapy", Journal of Clinical Hepatobiliary Diseases. vol. 32 No. 6, with English abstract. May 15, 2016, pp. 1-5.
Gao Yang et al., "Commonly used sclerosing agents to treat venous malformations that lead to nerves.", Journal of Tissue Engineering and Reconstructive Surgery. vol. 12 No. 4, with English abstract. Aug. 15, 2016, pp. 1-5.
Li Kai et al., "Foam sclerotherapy for venous malformations.", Advances in modern general surgery in China. Vol. 17 No. 9, Sep. 15, 2014, with English abstract. pp. 1-4.

(Continued)

*Primary Examiner* — Robert A Wax
*Assistant Examiner* — Quanglong N Truong
(74) *Attorney, Agent, or Firm* — JCIP GLOBAL INC.

(57) ABSTRACT

The present invention relates to an ethanol foam sclerosing agent for vascular anomalies and a preparation method thereof. The ethanol foam sclerosing agent includes absolute ethanol, water, Tween 80 and a stabilizer. The ethanol foam sclerosing agent further includes hyaluronic acid. The mass composition of the ethanol foam sclerosing agent includes 32-42% of absolute ethanol, 0.5-2% of Tween 80, 0-25% (excluding 0) of egg yolk lecithin, 0-2% (excluding 0) of hyaluronic acid, and the balance of water. The stabilizer is hyaluronic acid or glycerin. Foam is prepared by the Tessari method. While the original therapeutic effect of ethanol is not changed, the side effect of the ethanol is significantly reduced.

2 Claims, 4 Drawing Sheets

(56) References Cited

OTHER PUBLICATIONS

Wan Fengli et al., "Clinical Nursing of 16 Cases of Head and Neck Venous Malformation Treated by Foam Sclerotherapy.", Qilu Nursing Journal. Vol. 21 No. 6, Mar. 20, 2015, with English abstract. pp. 1-3.

"International Search Report (Form PCT/ISA/210) of PCT/CN2019/124643," mailed on Mar. 10, 2020, with English translation thereof, pp. 1-6.

\* cited by examiner

ETHANOL FOAM SCLEROSING AGENT FOR TREATING VASCULAR ANOMALIES AND PREPARATION METHOD THEREOF

CROSS-REFERENCE TO RELATED APPLICATION

This application is a 371 of international application of PCT application serial no. PCT/CN2019/124643, filed on Dec. 11, 2019, which claims the priority benefit of China application no. 201910450705.6, filed on May 28, 2019. The entirety of each of the above mentioned patent applications is hereby incorporated by reference herein and made a part of this specification.

BACKGROUND

Technical Field

The present invention belongs to the technical field of preparation of sclerosing agent materials, and specifically relates to an ethanol foam sclerosing agent for treating vascular anomalies and a preparation method thereof.

Description of Related Art

Information of the Related Art part is merely disclosed to increase the understanding of the overall background of the present invention, but is not necessarily regarded as acknowledging or suggesting, in any form, that the information constitutes the prior art known to a person of ordinary skill in the art.

Vascular anomalies are major diseases that seriously endanger human health, including venous malformations, arteriovenous malformations, hemangioma, lymphatic malformations and the like, among which venous malformations are the most common. Venous malformations can occur in any region of the human body, and about 60% occur in the maxillofacial region. Depending on the location and severity of the disease, on the one hand, the disease can seriously affect the appearance and function of the involved organs, and can be life-threatening due to complications such as infection, bleeding, and respiratory obstruction. On the other hand, the disease often requires life-long treatment, and its social harm is no less than that of malignant tumors.

The current international treatment strategy for venous malformations is comprehensive treatment based on sclerotherapy, combined with surgery, laser, interventional therapy, and other methods. The principle of sclerotherapy is to destroy the endothelial cells of the diseased blood/lymphatic vessels with drugs (sclerosing agents) to achieve the purpose of treatment. There are three commonly used sclerosing agents in clinical practice: anhydrous ethanol, polidocanol and bleomycin. Among them, anhydrous ethanol has the strongest sclerosing effect, but has the most serious side effects. In the sclerotherapy process, certain liquid sclerosing agent can be mixed with air to make foam to form a foam sclerosing agent. The latter has more advantages, such as better effect, more safety and fewer side effects than the liquid sclerosing agent, and the advantages are quite significant. Among the above three sclerosing agents, currently only polidocanol can be made into foam, while absolute ethanol and bleomycin cannot directly form foam with air. The inventor found that although absolute ethanol is recognized as the sclerosing agent with the strongest effect, its side effects are the most serious and the most frequent, mainly including tissue necrosis, which severely limits its wide application.

SUMMARY

In view of the problems in the prior art, the objective of the present invention is to provide an ethanol foam sclerosing agent for treating vascular anomalies and a preparation method thereof. The present invention provides a foamed ethanol sclerosing agent and a preparation method thereof, which can significantly reduce the side effects while not changing the original therapeutic effect.

In order to solve the above technical problems, the technical solution of the present invention is:

On the one hand, an ethanol foam sclerosing agent for vascular anomalies includes absolute ethanol, water and a non-ionic surfactant.

Vascular anomalies include venous malformations, arteriovenous malformations, lymphatic malformations, hemangioma and the like.

In some embodiments, the ethanol foam sclerosing agent further includes a stabilizer, and the stabilizer is hyaluronic acid or glycerin, preferably is hyaluronic acid.

The addition of the hyaluronic acid or glycerin to the ethanol foam sclerosing agent of the present invention can improve the stability of the ethanol foam sclerosing agent, improve the uniformity of the foam, extend the half-life of the foam, and ensure good stability.

In some embodiments, the non-ionic surfactant is composed of Tween and lecithin, preferably Tween 80 and egg yolk lecithin.

In some embodiments, the mass composition of the ethanol foam sclerosing agent includes 25-42% of absolute ethanol, 0.5-2% of Tween 80, 0-2% (excluding 0) of egg yolk lecithin, and the balance of water.

Foam is an aggregate of microbubbles formed by a large amount of gas dispersed in a small amount of liquid, and separated from each other by liquid films. Foam has a certain geometric shape, and is a tiny multiphase, viscous and unstable system. Pure liquids, such as water and ethanol, cannot form stable foam. Liquids that can form stable foam must contain two or more components.

Ethanol, with the molecular formula $C_2H_6O$, is the most common monohydric alcohol. Ethanol has surface activity, and the surface tension of an aqueous solution of ethanol gradually decreases with the concentration increases. Hydrogen bonds exist in the aqueous solution system of ethanol: when the mole fraction is 0-0.236 (volume fraction 0-50%), the association state of pure water is almost maintained between the molecules, and the association structure of water molecules dominates; when the mole fraction is 0.236-0.735 (volume fraction 50%-89%), the system has the strongest hydrogen bond association state; and when the mole fraction is 0.735-1.000 (volume fraction 89%-100%), the association state of pure ethanol is almost maintained between the molecules, and the association structure of ethanol molecules dominates. The inventor found that a 0-50% ethanol solution can be prepared into foam theoretically, but an ethanol solution with higher concentration cannot form foam. In practice, the concentration of an ethanol solution that can form foam is close to 50%, but a 50% ethanol solution cannot form foam.

Surfactants are a kind of substance with high surface activity. The surface tension of an aqueous solution of a surfactant drops sharply at low concentration, and the molecules are directionally aligned to form a certain structure, such as foam and micelles. The minimum concentration at which molecules form micelles in a solvent is the critical micelle concentration (cmc value). When the cmc value is reached, the surface tension of the solution drops to the lowest value, and the cmc value is an important indicator of the foaming ability of a surfactant. Surfactants are divided into ionic and non-ionic types. Non-ionic surfactants are widely used in pharmaceutics due to low toxicity and hemolytic action, stable chemical properties, compatibility with most drugs and the like, and are often used as solubilizer, dispersant, emulsifier, and suspending agent. Ethanol in a mixed solution will reduce the cmc value of a surfactant, but the combined use of two or more surfactants can improve the effect.

In some embodiments, the mass composition of the ethanol foam sclerosing agent includes 25-42% of absolute ethanol, 0.5-2% of Tween 80, 0-2% (excluding 0) of egg yolk lecithin, 0-2% (excluding 0) of hyaluronic acid, and the balance of water.

Further, the mass composition of the ethanol foam sclerosing agent is 33.3-40.5% of absolute ethanol, 0.6-0.7% of Tween 80, 0.9-1.1% of egg yolk lecithin, 0.7-1.5% of hyaluronic acid, and the balance of water.

Tween 80 and egg yolk lecithin have good biological safety, are internationally recognized pharmaceutical excipients, and are safe for low-dose intravenous injection.

As mentioned above, absolute ethanol cannot be directly mixed with air to prepare foam because ethanol does not have two polarities, i.e., hydrophilicity and hydrophobicity, but an ethanol solution can form air foam with the participation of non-ionic surfactants. The content of non-ionic surfactants has a certain influence on the stability of formed foam. Only when the content of the non-ionic surfactants matches with the concentration of ethanol can relatively stable foam be obtained. The formation mechanism of foam is that gas is dispersed in liquid to form a gas-liquid dispersion. The inventor found that the non-ionic surfactants in the above mass range and concentration range matching with the anhydrous ethanol in the above mass range can better foam. At the same time, the hyaluronic acid in the above mass range can be added to increase the foaming stability of the mixed solution, and the obtained foam has a uniform and stable texture and a longer half-life.

The effect of the egg yolk lecithin and the Tween 80 is that the two synergistically act to make ethanol foam. Addition of stabilizers exceeding the above range will increase the risk of side effects in foam treatment.

The effect of hyaluronic acid is that hyaluronic acid is a stabilizer and can improve the stability of the formed foam. The inventor found that addition of hyaluronic acid within a certain proportion range makes the foam uniform and dense and have a longer half-life, so that the applicability of the ethanol foam is better. The inventor believes that addition of a stabilizer exceeding the above range will reduce the ethanol concentration and affect the therapeutic effect.

On the other hand, a preparation method of the ethanol foam sclerosing agent includes the following specific steps:

mixing egg yolk lecithin, Tween 80, absolute ethanol and water to obtain a mixed solution A, and preparing ethanol foam according to the Tessari method.

In some embodiments, egg yolk lecithin, Tween 80, absolute ethanol, water and hyaluronic acid are mixed to obtain a mixed solution A, and ethanol foam is prepared according to the Tessari method.

In some embodiments, a process of preparing foam by the Tessari method is as follows: putting the mixed solution A into a syringe, drawing sterile air with another syringe, connecting the two syringes by a medical three-way valve, and mixing the mixed solution A and the sterile air into ethanol foam by performing injection back and forth several times according to the Tessari method.

Further, a volume ratio of the mixed solution A to the sterile air is 1:2-4.

Further, the preparation process is performed at room temperature.

The Tessari foaming method is: by performing injection back and forth through two syringes, gas and liquid are fully mixed to form foam. The mixed solution A of ethanol has a certain surface tension. When the gas breaks through the surface of the mixed solution, the surface tension of the mixed solution A decreases, forming a gas-liquid separation. If the gas inside the foam cannot break through the liquid film, the foam will exist stably. The volume ratio of the mixed solution A to air affects the stability of foam. Due to specificity of ethanol foam, the inventor found that the volume ratio of the mixed solution A to the sterile air within the above range can make the ethanol foam more stable.

Lecithin is known as the "third nutrient" alongside protein and vitamins, and is a mixture of phospholipids extracted from plants or animals through a physical processing method. Lecithin is generally referred to as the mixture of phospholipids. Lecithin is widely distributed in nature and rich in resources, and is a natural nutritional supplement with low price and high nutritional value and physiological functions. Lecithin has the main functions of improving the body's nerve dysfunction and disorder, restoring brain function, enhancing memory, preventing cardiovascular diseases, resisting aging and the like, and is widely used in the fields of medicine and food. In addition, lecithin is also a natural emulsifier and wetting agent, and is a non-ionic surfactant. In addition to its medical, nutritional and health-caring functions, lecithin is often used as an emulsifier for intravenous fat injection, with a general use concentration of 12 mg/ml. Lecithin is further divided into soybean lecithin and egg yolk lecithin. The lecithin used in the present invention is egg yolk lecithin for intravenous injection.

Tween 80 (polysorbate 80) is a non-ionic surfactant that can be used as an emulsifier, dispersant, solubilizer or stabilizer and the like, and is widely used in medicine, food and the like. The pharmacological effects and safety of Tween 80 have been thoroughly researched. Tween 80 for intravenous injection is used in the present invention.

Hyaluronic acid (HA) is a physiologically active substance widely existing in animals and human bodies, and is distributed in human skin, joint synovial fluid, umbilical cords, aqueous humor and vitreous bodies. Hyaluronic acid is a naturally degradable and absorbable biomedical material, has high viscoelasticity, plasticity, permeability, unique rheological properties, good biocompatibility and the like, and is widely used in the field of drug slow-release. Studies have reported that the application of hyaluronic acid in the treatment of vascular anomalies is safe and effective. A medical hyaluronic acid injection is used in the present invention.

The present invention has the following beneficial effects:

The present invention solves the problem that in the prior art, only absolute ethanol liquid can be used as a sclerosing agent. The inventor prepared an ethanol foam sclerosing agent, which has better effect, more safety and fewer side effects than liquid absolute alcohol.

The foam sclerosing agent prepared by the present invention has long half-life, convenient application, simple preparation method and good clinical application effect.

BRIEF DESCRIPTION OF THE DRAWINGS

The accompanying drawings of the specification forming a part of the present invention are used to provide further understanding of the present invention, and the exemplary embodiments of the present invention and descriptions thereof are used to explain the present invention but do not constitute an improper limitation on the present invention.

DESCRIPTION OF THE EMBODIMENTS

Figure 1:
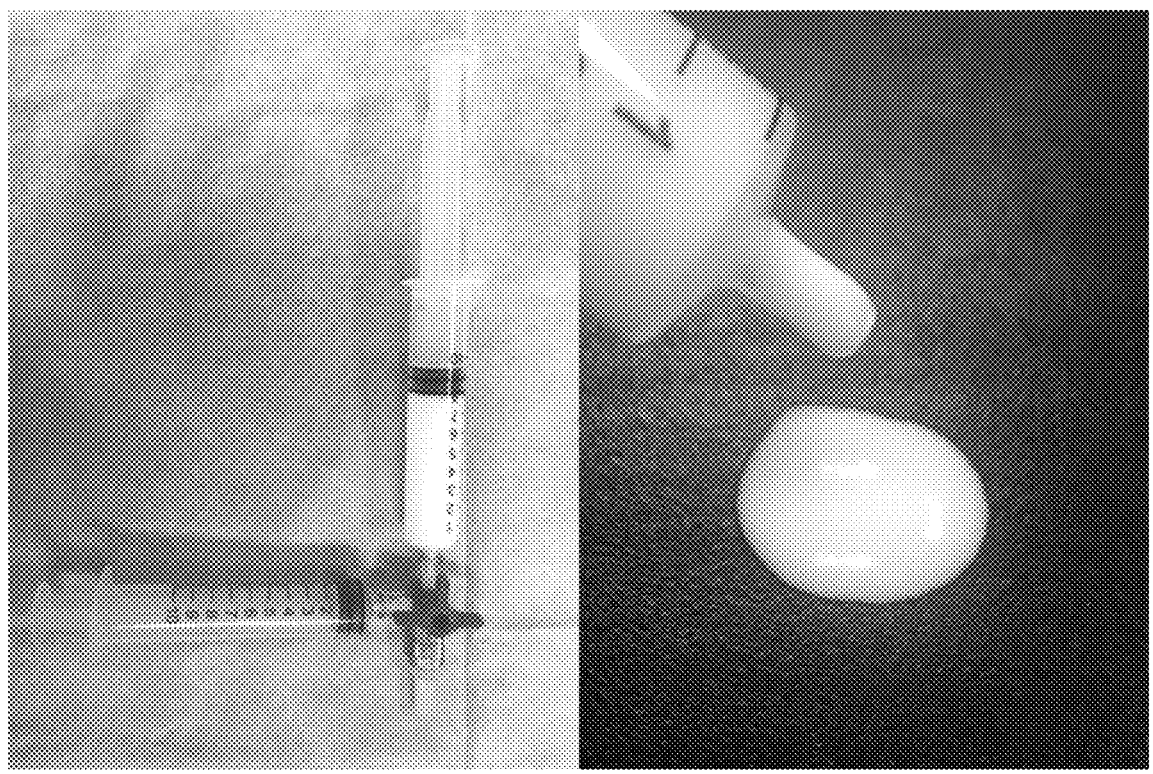
FIG. 1 is a schematic diagram of a preparation process of the Tessari method and a diagram of foam formed in Embodiment 5.

It should be pointed out that the following detailed descriptions are all illustrative and are intended to provide further descriptions of the present invention. Unless otherwise specified, all technical and scientific terms used herein have the same meanings as those usually understood by a person of ordinary skill in the art to which the present disclosure belongs.

It should be noted that terms used herein are only for describing specific implementations and are not intended to limit exemplary implementations according to this application. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

The present invention is further described below with reference to the embodiments.

Example 1

40.5 g of absolute ethanol, 56.7 g of water, 0.6 g of Tween 80, 1.1 g of egg yolk lecithin, and 1.1 g of hyaluronic acid were mixed. The mixed solution was drawn into a syringe, and sterile air was drawn with another syringe. At room temperature, ethanol foam was prepared by the clinically common foam production method—Tessari method according to a ratio of liquid:air=1:3. Uniform, stable and dense foam was formed, and the half-life of the foam was 1 min or longer.

Example 2

37.8 g of absolute ethanol, 59.9 g of water, 0.6 g of Tween 80, 1 g of egg yolk lecithin, and 0.7 g of hyaluronic acid were mixed. The mixed solution was drawn into a syringe, and sterile air was drawn with another syringe. At room temperature, ethanol foam was prepared by the clinically common foam production method—Tessari method according to a ratio of liquid:air=1:3. Uniform, stable and dense foam was formed, and the half-life of the foam was 1 min or longer.

Example 3

35 g of absolute ethanol, 62.6 g of water, 0.6 g of Tween 80, 1.1 g of egg yolk lecithin, and 0.7 g of hyaluronic acid were mixed. The mixed solution was drawn into a syringe, and sterile air was drawn with another syringe. At room temperature, ethanol foam was prepared by the clinically common foam production method—Tessari method according to a ratio of liquid:air=1:3. Uniform, stable and dense foam was formed, and the half-life of the foam was 1 min or longer.

Example 4

33.3 g of absolute ethanol, 64.4 g of water, 0.7 g of Tween 80, 0.9 g of egg yolk lecithin, and 0.7 g of hyaluronic acid were mixed. The mixed solution was drawn into a syringe, and sterile air was drawn with another syringe. At room temperature, ethanol foam was prepared by the clinically common foam production method—Tessari method according to a ratio of liquid:air=1:3. Uniform, stable and dense foam was formed, and the half-life of the foam was 1 min or longer.

Example 5

40.5 g of absolute ethanol, 56.3 g of water, 0.6 g of Tween 80, 1.1 g of egg yolk lecithin, and 1.5 g of hyaluronic acid were mixed. The mixed solution was drawn into a syringe, and sterile air was drawn with another syringe. At room temperature, ethanol foam was prepared by the clinically common foam production method—Tessari method according to a ratio of liquid:air=1:3. Uniform, stable and dense foam was formed, and the half-life of the foam was longer than that in Embodiment 1.

FIG. 1 shows a schematic diagram of the preparing process of the ethanol foam and a diagram of the prepared foam. It can be seen that the ethanol foam is tiny emulsified foam.

Comparative Example 1

The difference from Embodiment 1 is that Tween 80 was not added and 1.7 g of egg yolk lecithin was added. As a result, the solution could not form foam.

Comparative Example 2

The difference from Embodiment 1 is that egg yolk lecithin was not added and 1.7 g of Tween 80 was added. As a result, the solution could not form foam.

Comparative Example 3

The difference from Embodiment 1 is that absolute ethanol was 50 g and water was 47.2 g. As a result, the solution could not form foam.

Experimental Example 1

Figure 2:
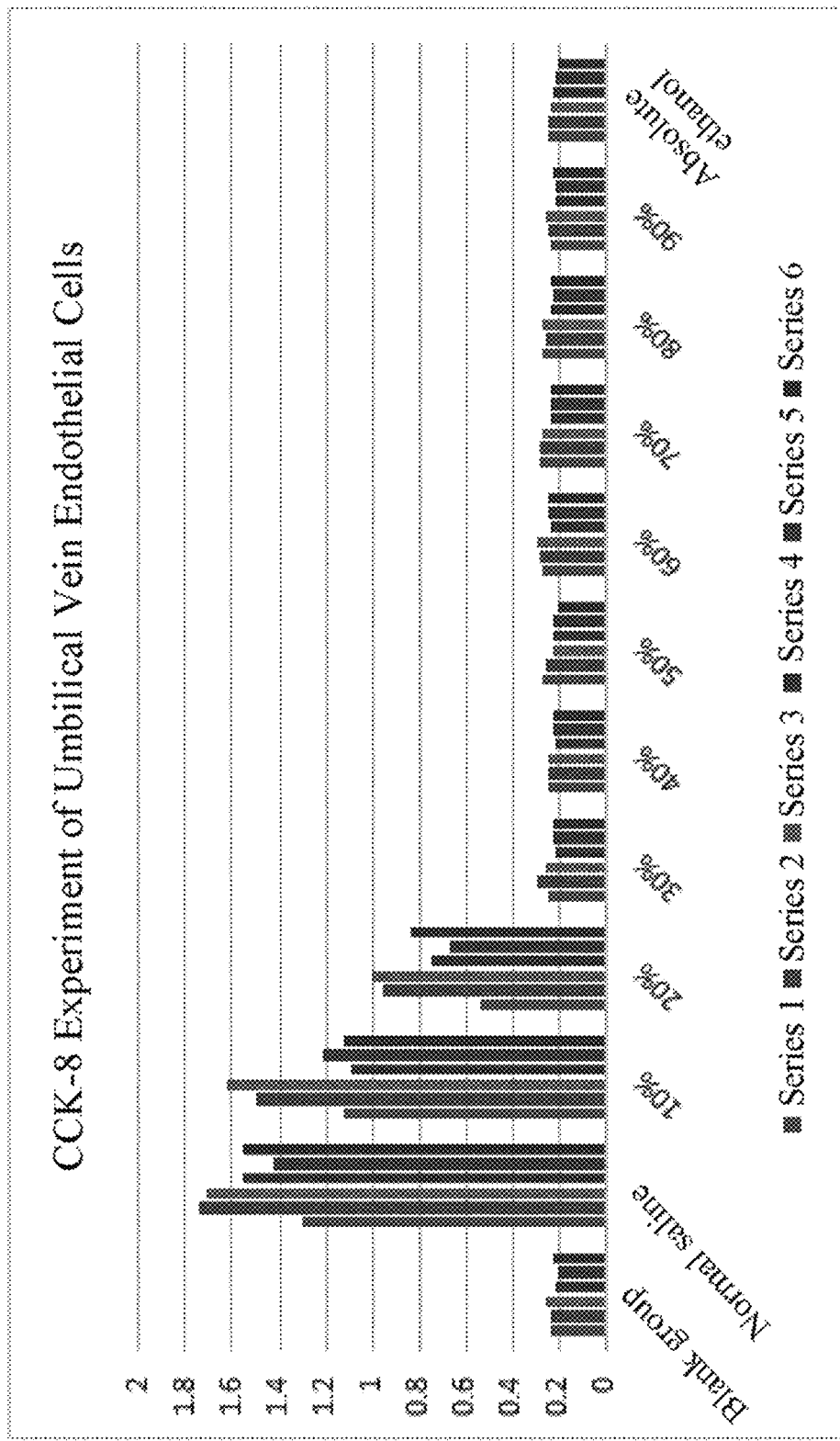
FIG. 2 is a CCK8 cell experiment diagram in Experimental example 1.

Cell experiment: A CCK8 cell experiment was performed with ethanol aqueous solutions of different concentrations. The cells were umbilical vein endothelial cells. The experiment included a blank group (no cells), a control group (normal saline and absolute ethanol), and an experimental group (the volume fractions of ethanol aqueous solutions were 10%, 20%, 30%, 40%, 50%, 60%, 70%, 80%, and 90% respectively). The specific curve is shown in FIG. 2. Each group in the figure includes series 1 to series 6 from left to right, and the series 1 to series 6 refer to the results obtained by performing the experiment six times under the same experimental conditions. The results obtained show that ethanol aqueous solutions with the volume fraction of 30-100% has a good destructive ability and can cause necrosis of the umbilical vein endothelial cells. Considering the experimental error and blood dilution effect, the present invention maximizes the concentration of ethanol in the mixed solution.

Experimental Example 2

Figure 3:
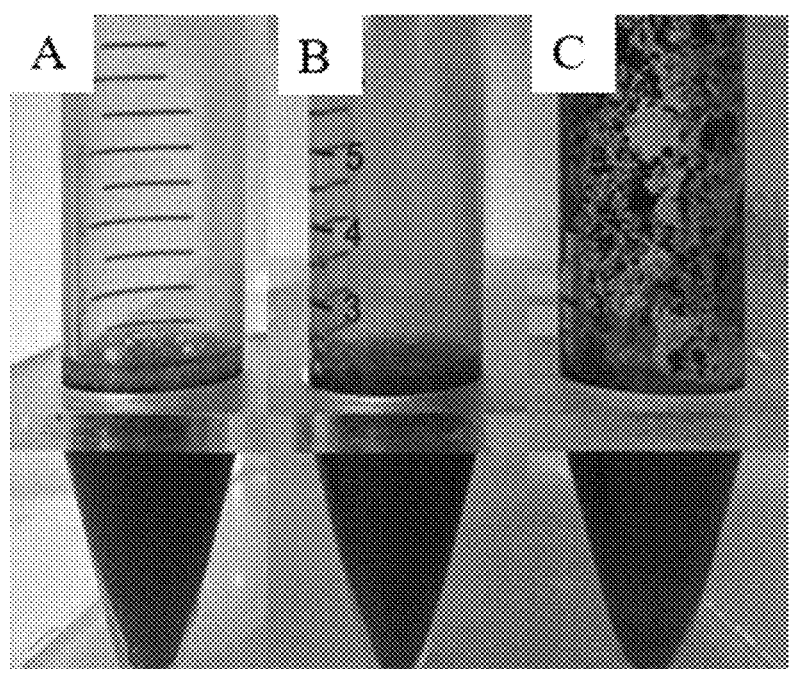
FIG. 3 is a picture of plasma experiment of Experimental example 2, wherein A is fresh human anticoagulant blood, B is human anticoagulant blood after a sclerosing agent of Embodiment 1 is added, and C is human anticoagulant blood after absolute ethanol is added.

Plasma experiment: A plasma experiment was performed using absolute ethanol and the sclerosing agent solution of Embodiment 1. As shown in A of FIG. 3, 1 mL of fresh human anticoagulant blood was taken. As shown in C of FIG. 3, absolute ethanol was added to a test tube, and as shown in B of FIG. 3, the sclerosing agent solution of Embodiment 1 was added to a test tube. As shown in C of FIG. 3, a large amount of reddish-brown solid substance was immediately formed in the test tube, which indicated that the absolute ethanol coagulated the protein in the plasma. As shown in B of FIG. 3, the blood color in the test tube became slightly darker, but no obvious solid precipitation was separated, which indicated that the sclerosing agent obtained in Embodiment 1 did not coagulate the protein in the plasma.

Experimental Example 3

Animal experiment: A first experimental group: the experimental subjects were 20 New Zealand white rabbits with the body weight of 1.5 kg, injected with 0.5 mL of absolute ethanol solution. A second experimental group: the experimental subjects were 20 New Zealand white rabbits with the body weight of 1.5 kg, injected with 0.5 mL of the foam sclerosing agent of Embodiment 1. The edges of ears of the experimental subjects in the first experimental group and the second experimental group were all intact before the experiment.

Figure 4:
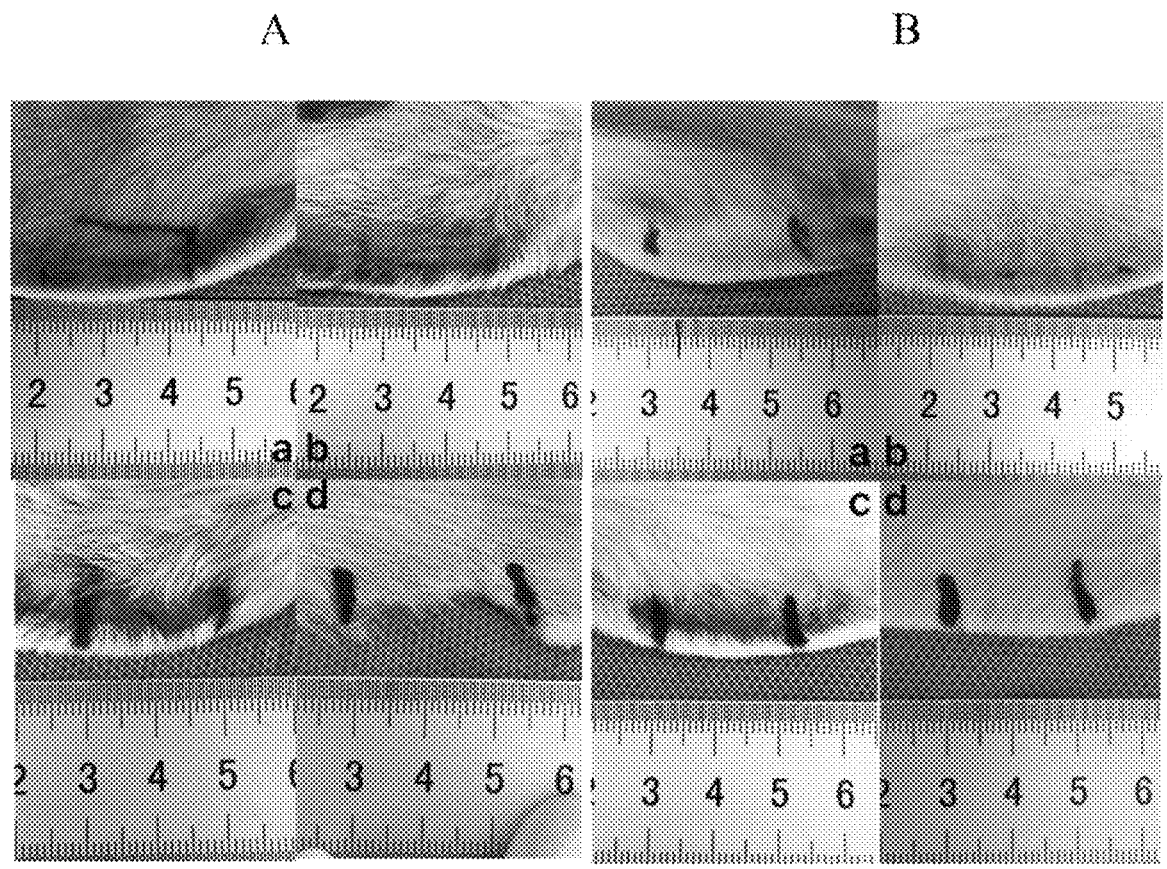
FIG. 4 is an animal experiment picture of Experimental example 3, wherein A and B are comparison pictures of ear edge experiment of two groups of New Zealand white rabbits, A is a group with the injection of absolute ethanol, and B is a group with the injection of a foam sclerosing agent of Embodiment 1.

The results of the first experimental group are shown in A of FIG. 4, wherein a is the reaction immediately after the injection, which shows that extensive and large-area hematoma appears on the ear edge immediately; b is the reaction 3 days after the injection, which shows that the whole ear has obvious hematoma; c is the reaction 7 days after the injection, which shows that the swelling is reduced; and d is the reaction 25 days after the injection, which shows that the local blood vessels and some normal tissues are destroyed, resulting in tissue defect of the rabbit ear edge. The results of the second experimental group are shown in B of FIG. 4, wherein a is the reaction immediately after the injection, which shows that the tube cavity is filled with the foam sclerosing agent, and no significant anomaly is seen around the tube; b is the reaction 3 days after the injection, which shows that local hematoma appears, and compared with the group with the injection of absolute ethanol, the symptom is milder; c is the reaction 7 days after the injection, which shows that the hematoma basically subsides, and only the inflammation around the ear veins is significant; and d is the reaction 25 days after the injection, which shows that the hematoma disappeared, and the local normal tissues have no significant changes.

The results show that the foam sclerosing agent of the present invention has slight side effects on local normal tissues.

Experimental Example 4

Clinical research: Patient's main complaint, diagnosis, treatment methods, and treatment effects are as follows:

Patient 1

Female, 57 years old. Medical history: Facial swelling since childhood, worsening in the past 5 years, and tongue hypertrophy, affecting language and eating, accompanied by snoring. Diagnosis: Giant venous malformations in the face and neck. Treatment method: Sclerotherapy with the ethanol foam of Embodiment 2, once a month, about 10 ml each time. After 3 months, the sclerotherapy has significant effects. After the texture of the lesion becomes tougher, surgical repair is considered.

Patient 2

Male, 25 years old. Medical history: Facial swelling for 20 years, gradually worsening. Treatment method: Sclerotherapy with the ethanol foam of Embodiment 2, once a month, 2 times in total, about 5 ml each time. After 2 months, the sclerotherapy effect is significant.

Patient 3

Female, 19 years old. Medical history: Heaviness of the right lower extremity for 10 years, worsening during exercise. Diagnosis: Venous malformation of the right lower extremity. Treatment method: Sclerotherapy with the ethanol foam of Embodiment 2, once a month, about 10 ml each time. After 2 months, the symptoms improved significantly. Treatment was continued when symptoms worsen.

Patient 4

Male, 32 years old. Medical history: A mass appeared on the glans when the penis was erected, affecting the sexual life of the patient after marriage. Diagnosis: Glans venous malformation. Treatment method: Sclerotherapy with the ethanol foam of Embodiment 2, once, 1 ml. The patient has been cured.

Patient 5

Female, 22 years old. Medical history: Lateral lingual mass for 2 years. Diagnosis: Lingual venous malformation. Treatment method: Sclerotherapy with the ethanol foam of Embodiment 2, once, 1 ml. The patient has been cured.

Patient 6

Female, 70 years old. Medical history: Lower lip mass for more than 50 years, recently worsening. Diagnosis: Lower lip venous malformation. Treatment method: Sclerotherapy with the ethanol foam of Embodiment 2, once, 0.5 ml. A good therapeutic effect was achieved, and the patient has been cured.

Patient 7

Female, 60 years old. Medical history: Mouth floor swelling for more than 40 years. Diagnosis: Mouth floor venous malformation. Treatment method: Sclerotherapy with the ethanol foam of Embodiment 2, once a month, 2 times in total, about 10 ml each time. The patient has been cured.

Patient 8

Female, 50 years old. Medical history: Repeated swelling of the tongue body for more than 30 years. Diagnosis: Lingual venous malformation. Treatment method: Sclerotherapy with the ethanol foam of Embodiment 2, once a month, 2 times in total, about 2 ml each time. The patient has been cured.

Patient 9

Male, 66 years old. Medical history: Tongue mass for 1 year. Diagnosis: Lingual venous malformation. Treatment method: Sclerotherapy with the ethanol foam of Embodiment 2, once, 1 ml. The patient has been cured.

Patient 10

Female, 53 years old. Medical history: Facial swelling for 40 years. Diagnosis: Upper lip venous malformation. Treatment method: Sclerotherapy with the ethanol foam of Embodiment 2, once a month, about 10 ml for the first time, and about 5 ml for the second time. The patient has been cured.

Patient 11

Female, 58 years old. Medical history: Mass in the right neck region for more than 10 years. Diagnosis: Venous malformation type IV in the right neck region. Treatment method: Sclerotherapy with the ethanol foam of Embodiment 2 under DSA, once a month, 3 times in total, about 8 ml each time. A good therapeutic effect was achieved, and the patient has been cured.

Patient 12

Male, 61 years old. Medical history: Tongue mass for half a year. Diagnosis: Right lingual venous malformation. Treatment method: Sclerotherapy with the ethanol foam of Embodiment 2, once, 1 ml. The patient has been cured.

Patient 13

Male, 25 years old. Medical history: Paraesthesia pharyngitis for 10 years. Diagnosis: Soft palate venous malformation. Treatment method: Sclerotherapy with the ethanol foam of Embodiment 2, once a month, 2 times in total, about 5 ml each time. The patient has been cured.

Patient 14

Female, 30 years old. Medical history: Upper lip mass for 20 years. Diagnosis: Upper lip venous malformation. Treatment method: Sclerotherapy with the ethanol foam of Embodiment 2, once, 3 ml. The patient has been cured.

Patient 15

Male, 39 years old. Medical history: Chin mass for 30 years. Diagnosis: Lower lip venous malformation. Treatment method: Sclerotherapy with the ethanol foam of Embodiment 2, once a month, 3 times in total, about 10 ml each time. The patient has been cured.

Patient 16

Male, 14 years old. Medical history: Swelling of face, neck and chest for several years. Diagnosis: Venous malformations in the face, neck and chest. Treatment method: Sclerotherapy with the ethanol foam of Embodiment 2, once a month, 3 times in total, about 10 ml each time. A good treatment effect was achieved, and the patient has been cured.

Patient 17

Male, 48 years old. Medical history: Right cheek swelling for 5 years. Diagnosis: Right cheek venous malformation. Treatment method: Sclerotherapy with the ethanol foam of Embodiment 2, once, 2 ml. The patient has been cured.

Patient 18

Female, 47 years old. Medical history: Swelling of the left face region for about 1 year after trauma. Diagnosis: Traumatic venous malformation of the left face region. Treatment method: Sclerotherapy with the ethanol foam of Embodiment 2, once, 3 ml. The patient has been cured.

Patient 19

Male, 16 years old. Medical history: Left parotid region swelling for 1 year. Diagnosis: Venous malformation in the left parotid region. Treatment method: Sclerotherapy with the ethanol foam of Embodiment 2, once, 3 ml. The therapeutic effect was significant and the patient has been cured.

Patient 20

Female, 49 years old. Medical history: Tongue body swelling for more than 40 years. Diagnosis: Venous malformations in tongue and mouth floor. Treatment method: Sclerotherapy with the ethanol foam of Embodiment 2, once a month, 3 times in total, about 6 ml each time. Good therapeutic effects were achieved, and the patient has been cured.

Patient 21

Female, 32 years old. Medical history: Mouth floor swelling for more than 20 years. Diagnosis: Venous malformations in the mouth floor and neck. Treatment method: Sclerotherapy with the ethanol foam of Embodiment 2, once a month, 3 times in total, about 6 ml each time. A good effect was achieved, and the patient has been cured.

Patient 22

Male, 47 years old. Medical history: Swelling in the left temporal region for 3 years. Diagnosis: Venous malformation in the left temporal region. Treatment method: Sclerotherapy with the ethanol foam of Embodiment 2, once, 4 ml. The therapeutic effect was significant, and the patient has been cured.

Patient 23

Female, 66 years old. Medical history: Lower lip swelling for 3 years, gradually worsening. Diagnosis: Lower lip venous malformation. Treatment method: Sclerotherapy with the ethanol foam of Embodiment 2, once, 4 ml. The therapeutic effect was significant, and the patient has been cured.

The foam sclerosing agent of the present invention has a good treatment effect on various venous malformations, the treatment process is simple, the treatment effect is significant, and the foam sclerosing agent has no obvious adverse reaction and is safe and effective.

The foregoing descriptions are merely preferred embodiments of the present invention, but are not intended to limit the present invention. A person skilled in the art may make various alterations and variations to the present invention. Any modification, equivalent replacement, or improvement made and the like within the spirit and principle of the present invention shall fall within the protection scope of the present invention.

What is claimed is:

1. An ethanol foam sclerosing agent for vascular anomalies, with a mass composition comprising 25-42% of absolute ethanol, 0.5-2% of polysorbate 80, 0-2% (excluding 0) of egg yolk lecithin, 0-2% (excluding 0) of hyaluronic acid, and the balance of water.

2. The ethanol foam sclerosing agent of claim 1, wherein the mass composition of the ethanol foam sclerosing agent comprises 33.3-40.5% of absolute ethanol, 0.6-0.7% of polysorbate 80, 0.9-1.1% of egg yolk lecithin, 0-2% (excluding 0) of hyaluronic acid, and the balance of water.

* * * * *